United States Patent
Sawada et al.

(10) Patent No.: US 11,583,307 B2
(45) Date of Patent: Feb. 21, 2023

(54) ULTRASONIC TRANSMITTER UNIT

(71) Applicant: OLYMPUS CORPORATION, Hachioji (JP)

(72) Inventors: Kiichiro Sawada, Hachioji (JP); Hiroyuki Araki, Hachioji (JP); Naoki Narumi, Kunitachi (JP)

(73) Assignee: OLYMPUS CORPORATION, Tokyo (JP)

( * ) Notice: Subject to any disclaimer, the term of this patent is extended or adjusted under 35 U.S.C. 154(b) by 272 days.

(21) Appl. No.: 15/930,654

(22) Filed: May 13, 2020

(65) Prior Publication Data

US 2020/0268406 A1   Aug. 27, 2020

Related U.S. Application Data

(63) Continuation of application No. PCT/JP2017/041534, filed on Nov. 17, 2017.

(51) Int. Cl.
*A61B 17/32* (2006.01)
*A61B 17/16* (2006.01)

(52) U.S. Cl.
CPC .. *A61B 17/320068* (2013.01); *A61B 17/1675* (2013.01); *A61B 17/320016* (2013.01); *A61B 2017/320073* (2017.08)

(58) Field of Classification Search
CPC .............................................. A61B 17/320068
See application file for complete search history.

(56) References Cited

U.S. PATENT DOCUMENTS

2005/0245823 A1 * 11/2005 Tsuchiya .......... A61B 17/22012
600/439

FOREIGN PATENT DOCUMENTS

| JP | H10-005237 A | 1/1998 |
|----|-------------|---------|
| JP | 2001-079013 A | 3/2001 |
| JP | 2005-312675 A | 11/2005 |
| WO | 2006/030563 A1 | 3/2006 |
| WO | 2017/013813 A1 | 1/2017 |
| WO | 2017/013815 A1 | 1/2017 |

OTHER PUBLICATIONS

May 19, 2020 International Preliminary Report on Patentability issued in Application No. PCT/JP2017/041534.
Feb. 6, 2018 International Search Report Issued in Japanese Patent Application PCT/JP2017/041534.

* cited by examiner

*Primary Examiner* — Olivia C Chang
(74) *Attorney, Agent, or Firm* — Oliff PLC

(57) ABSTRACT

An ultrasonic transmitter unit includes: a sheath that forms a cylindrical shape and is having a proximal end and a distal end; an ultrasonic transmitter configured to be inserted into the sheath; and a cover member that covers a part of the ultrasonic transmitter and has an inner surface and an outer surface. The ultrasonic transmitter includes: a first area surrounded by the sheath; a second area protruding from the distal end of the sheath; and a distal-end treatment portion provided in a distal end of the second area. The cover member covers the second area of the ultrasonic transmitter, and exposes the distal-end treatment portion of the ultrasonic transmitter to an outside, and is made of fluorine-based resin.

15 Claims, 9 Drawing Sheets

ULTRASONIC TRANSMITTER UNIT

CROSS-REFERENCE TO RELATED APPLICATIONS

This is a Continuation Application of PCT Application No. PCT/JP2017/041534, filed Nov. 17, 2017, the entire contents of which are incorporated herein by reference.

BACKGROUND

International Publication No. WO2017/0013815 A1 discloses an ultrasonic treatment instrument which cuts a treatment target such as a bone, etc., using ultrasonic vibration. The aforementioned ultrasonic treatment instrument includes a sheath extended along the longitudinal axis, and an ultrasonic probe is inserted into the sheath. The ultrasonic probe has its proximal end connected to an ultrasonic transducer, and includes a distal-end treatment portion in a protrusion from the sheath toward a distal side. Ultrasonic vibration generated in the ultrasonic transducer is transmitted through the ultrasonic probe to its distal-end treatment portion. The distal-end treatment portion to which ultrasonic vibration has been transmitted is used to cut a treatment target.

In the treatment, an ultrasonic treatment instrument such as that disclosed in International Publication No. WO2017/0013815 A1 is used with another instrument such as an arthroscope (endoscope) in combination with the ultrasonic treatment instrument within a joint cavity in a human body. In such a case, the sheath may be extended up to the vicinity of the distal-end treatment portion in order to prevent contact between the ultrasonic probe and another instrument (external instrument). The sheath extended up to the vicinity of the distal-end treatment portion may affect treatment performance such as accessibility to a treatment target.

SUMMARY

Exemplary embodiments relate to an ultrasonic nit used for an ultrasonic treatment instrument that can treat a treatment target such as a bone, etc., using ultrasonic vibration. According to an exemplary embodiment, an ultrasonic transmitter unit can include: a sheath that forms a cylindrical shape and is having a proximal end and a distal end; an ultrasonic transmitter configured to be inserted into the sheath; and a cover member that covers a part of the ultrasonic transmitter and has an inner surface and an outer surface. The ultrasonic transmitter can include: a first area surrounded by the sheath; a second area protruding from the distal end of the sheath; and a distal-end treatment portion provided in a distal end of the second area. The cover member covers the second area of the ultrasonic transmitter, and exposes the distal-end treatment portion of the ultrasonic transmitter to an outside, and is made of fluorine-based resin.

DETAILED DESCRIPTION

A first exemplary embodiment will be described with reference to FIGS. 1 to 11.

Figure 1:
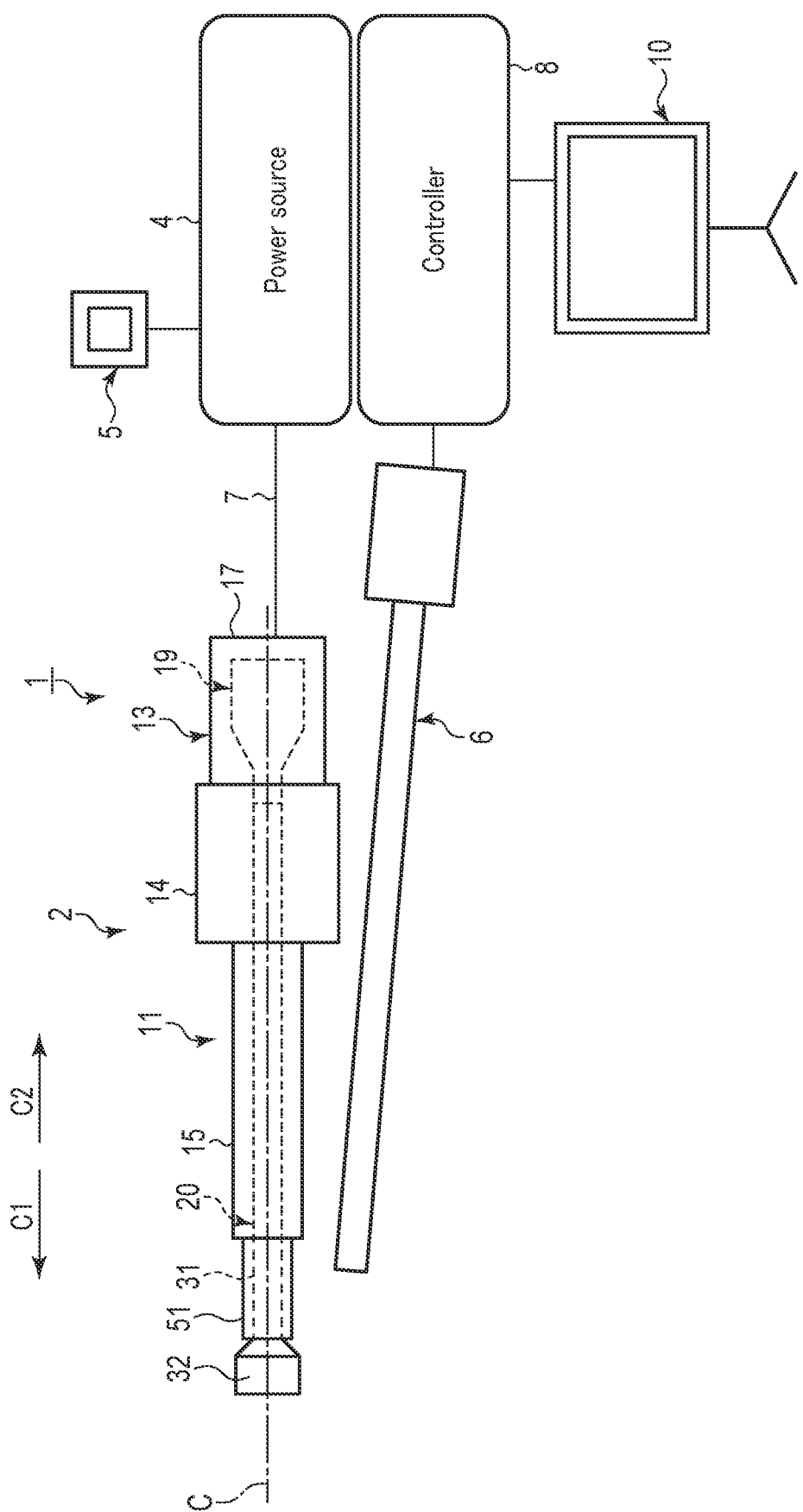
FIG. 1 is a view schematically showing a treatment system according to a first exemplary embodiment.

FIG. 1 is a view showing a treatment system 1. The treatment system 1 according to the present embodiment is used for a treatment in which, for example, a hole (bone hole) is formed in a bone within a patient's knee joint. As shown in FIG. 1, the treatment system 1 includes an ultrasonic treatment assembly 2, a power supply 4, an arthroscope (endoscope) 6, a controller 8, and a monitor 10.

The arthroscope 6 is an observation device configured to observe an inside of a knee joint, that is, an inside of a joint cavity. The controller 8 retrieves images obtained by the arthroscope 6, and performs image processing. The monitor 10 displays images (videos) generated through the image processing by the controller 8. For example, if treatment is performed by making a direct visual observation of a treatment target region, the treatment system 1 does not necessarily require the arthroscope (endoscope) 6.

The ultrasonic treatment assembly 2 includes a treatment instrument 11 and a transducer unit 13. The treatment instrument 11 and the transducer unit 13 are detachably attached to each other. The treatment instrument 11 or the ultrasonic treatment assembly 2 including the treatment instrument 11 and the transducer unit 13 is the ultrasonic treatment instrument according to the present embodiment. The treatment instrument 11 is an example of an ultrasonic transmitter unit.

The treatment instrument 11 includes a housing (handle) 14, a cylindrical sheath (outer pipe) 15 coupled to the housing 14, and an ultrasonic probe (ultrasonic transmitter) 20 inserted into the sheath 15. The housing 14 is holdable. The sheath 15 defines longitudinal axis C. Herein, a direction extending along the longitudinal axis C is referred to as a longitudinal direction. One side in the longitudinal direction is referred to as a distal side (side indicated by arrow C1 in FIG. 1), and the side opposite to the distal side is referred to as a proximal side (side indicated by arrow C2 in FIG. 1). The sheath 15 is extended from the proximal side to the distal side along the longitudinal axis C, and is coupled to the distal side of the housing 14.

The transducer unit 13 includes a transducer case 17. One end of a cable 7 is connected to the transducer case 17. The other end of the cable 7 is detachably connected to the power supply 4. An ultrasonic transducer 19 is provided inside the transducer case 17. The ultrasonic transducer 19 is, for example, a bolt-clamped Langevin-type ultrasonic transducer. The ultrasonic transducer 19 is electrically connected to the power supply 4 through an electric pathway extended through the inside of the transducer case 17 and the inside of the cable 7.

The ultrasonic probe (vibration transmitter) 20 is arranged inside the housing 14. The ultrasonic probe 20 is extended along the longitudinal axis C. The ultrasonic probe 20 is made of a material through which ultrasonic vibration can be transmitted along the longitudinal axis C. The ultrasonic probe 20 is made of, e.g., a metal material such as a titanium alloy.

The ultrasonic probe 20 includes a probe main body 31 extended along the longitudinal axis C. The proximal end portion of the probe main body 31 is connected to the ultrasonic transducer 19 from the distal side. The probe main body 31 is extended from the inside of the housing 14 toward the distal side, and runs through the inside of the sheath 15 to protrude from the distal end of the sheath 15 toward the distal side.

A distal-end treatment portion 32 is provided on the distal end portion of the ultrasonic probe 20. The distal-end treatment portion 32 is provided on the distal side relative to the probe main body 31. The distal-end treatment portion 32 is provided on a protrusion of the ultrasonic probe 20, which protrudes from the distal end of the sheath 15 toward the distal side. The distal-end treatment portion 32 is formed into a block shape and cuts a treatment target by transmitted ultrasonic vibration. This enables the distal-end treatment portion 32 to form a hole (bone hole) in a bone as a treatment target, by ultrasonic vibration.

The power supply 4 includes an ultrasonic power supply. The ultrasonic power supply includes a waveform generator, a conversion circuit, a transformer, etc., and converts a power from a battery power supply, a receptacle power supply, etc., into an AC power. By the ultrasonic power supply supplying electric energy (AC power) to the transducer unit 13, ultrasonic vibration is generated in the ultrasonic transducer 19. At this time, the ultrasonic transducer 19 generates longitudinal vibration with an appropriate amplitude along the longitudinal axis C. Ultrasonic vibration generated in the ultrasonic transducer 19 is transmitted to the proximal end portion of the ultrasonic probe 20. The transmitted ultrasonic vibration is transmitted to the distal-end treatment portion 32 through the ultrasonic probe 20 from the proximal side to the distal side.

A switch 5 is connected to the power supply 4. The switch 5 is an energy operation inputting section. By inputting operation with the switch 5, the power supply 4 supplies electric energy to the transducer unit 13, resulting in the generation of ultrasonic vibration in the ultrasonic transducer 19. Operation is input by, for example, pressing the switch 5, and release of the pressing cancels the state in which operation has been input. It is also preferable that the switch 5 be provided on the housing 14.

A shape including a length and a diameter, and a material are set as appropriate for the ultrasonic probe 20 in such a manner as to vibrate at a resonance frequency of the ultrasonic transducer 19 and a frequency of output from the power supply 4. It is preferable that a total length of a vibrator including the ultrasonic transducer 19 and the ultrasonic probe 20 be, for example, the integral multiple of a half wavelength of ultrasonic vibration to be transmitted. A half wavelength of ultrasonic vibration depends on a resonance frequency of the vibrator including the ultrasonic transducer 19 and the ultrasonic probe 20. In an embodiment, the vibrator including the ultrasonic transducer 19 and the ultrasonic probe 20 vibrates at a resonance frequency ranging from, e.g., 46 kHz to 48 kHz, and preferably at a resonance frequency ranging from 46.5 kHz to 47.5 kHz.

With the ultrasonic probe 20 being ultrasonic-vibrating, the proximal end of the probe main body 31 and the distal end of the distal-end treatment portion 32 function as vibration anti-nodes in the ultrasonic probe 20.

The probe main body 31 is supported at positions of vibration nodes with respect to the housing 14.

Figure 2:
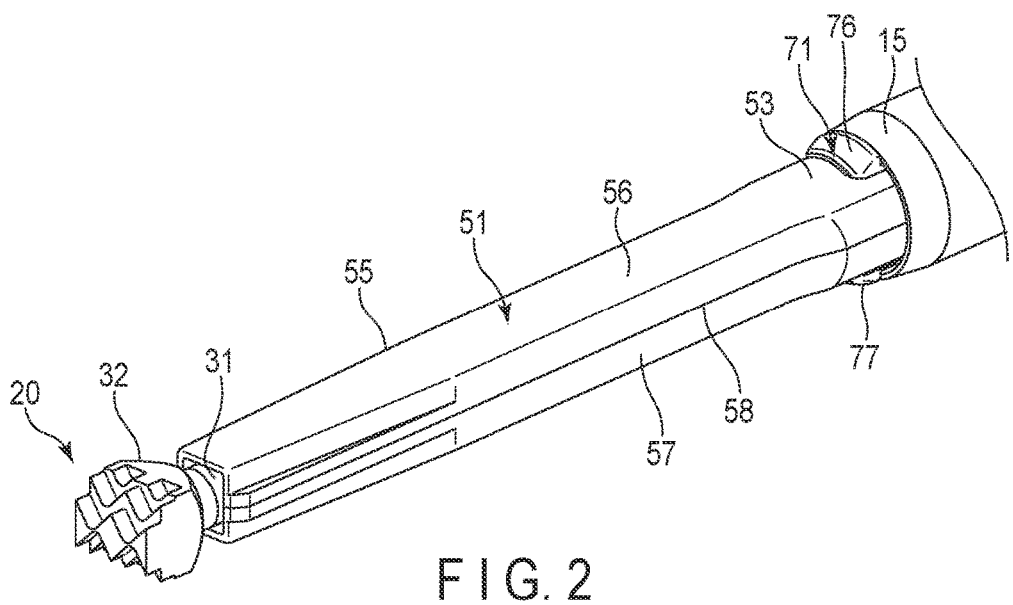
FIG. 2 is a perspective view schematically showing a distal end portion of an ultrasonic treatment instrument according to a first exemplary embodiment.
Figure 3A:
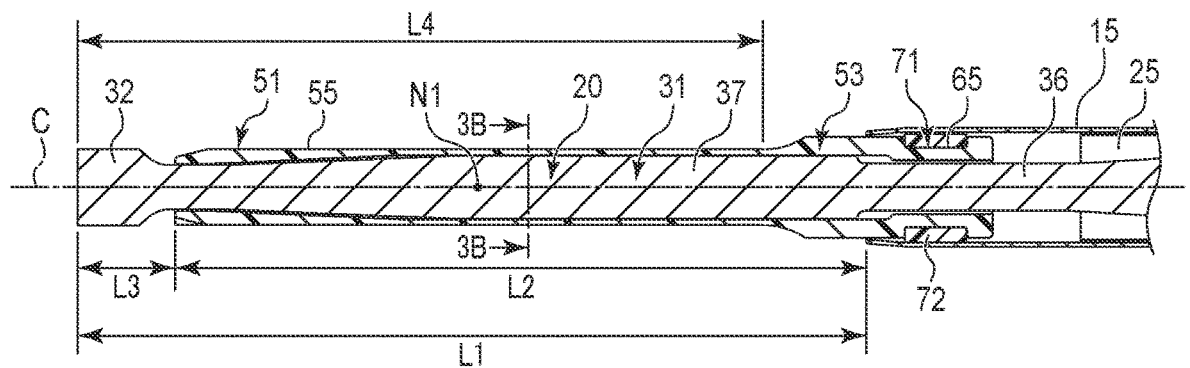
FIG. 3A is a view schematically showing the distal end portion of the ultrasonic treatment instrument according to a first exemplary embodiment, in a cross section which is parallel or substantially parallel to and also passes through a longitudinal axis.

As shown in FIGS. 2 and 3A, the probe main body 31 includes a first area 36 and a second area 37. The first area 36 is arranged inside the sheath 15 or the housing 14.

The second area 37 is positioned on the distal side relative to the first area 36, and protrudes from the distal end of the sheath 15 toward further the distal side. The first area 36 is extended from the proximal end of the probe main body 31 toward the distal side, and the proximal end of the first area 36 forms the proximal end of the ultrasonic probe 20. The proximal end of the second area 37 is continuous with the distal end of the first area 36. The distal end of the second area 37 is continuous with the proximal end of the distal-end treatment portion 32.

An inner tube 25 is arranged between the outer peripheral surface of the first area 36 of the probe main body 31 and the sheath 15. The inner tube 25 is supported by the inner peripheral surface of the sheath 15. With the inner tube 25 being provided between the ultrasonic probe 20 and the sheath 15, the ultrasonic probe 20 and the sheath 15 are prevented from coming into contact with each other.

In the longitudinal direction, the length of the protrusion of the ultrasonic probe 20, which protrudes from the distal end of the sheath 15 toward the distal side, is set to length L1. Length L1 is equal to a sum of L2 in the longitudinal direction of the second area 37 of the probe main body 31 and length L3 in the longitudinal direction of the distal-end treatment portion 32. Length L1 ranges from 20 mm to 70 mm. Preferably, length L1 ranges from 35 mm to 60 mm. Length L1 is set as appropriate in accordance with a size of a joint cavity, a depth of a bone hole, etc., which will be described later.

Among vibration nodes when the ultrasonic probe 20 is ultrasonic-vibrating, vibration node N1, which is the first node from the distal side, is positioned within a range of the second area 37 of the probe main body 31 of the ultrasonic probe 20. That is, the node N1 as the first node from the distal side is positioned in the protrusion of the ultrasonic probe 20, which protrudes from the distal end of the sheath 15 toward the distal side.

Figure 3B:
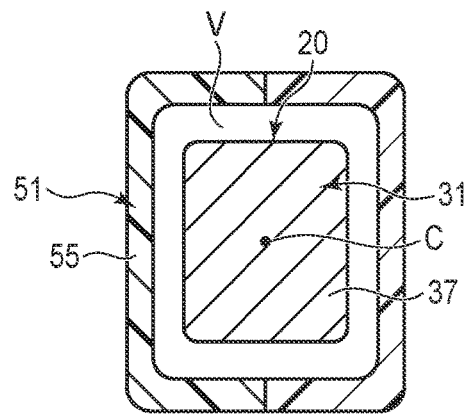
FIG. 3B is a cross-sectional view taken along line 3B-3B shown in FIG. 3A.
Figure 4:
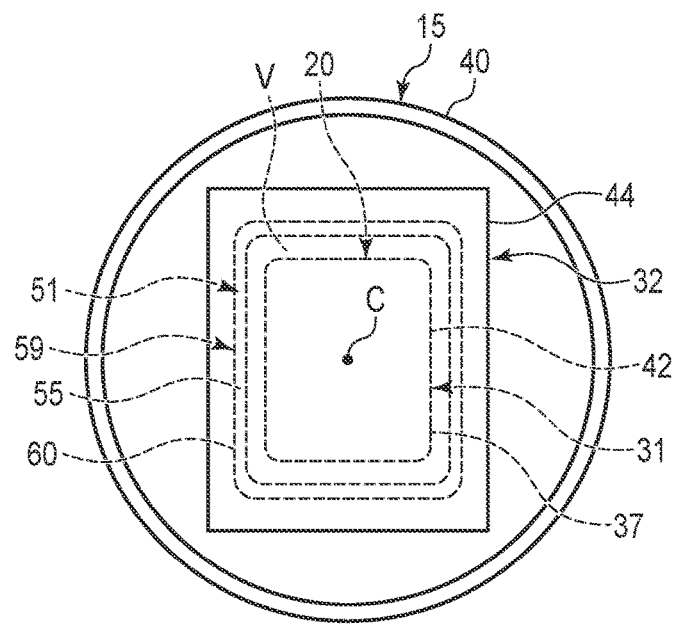
FIG. 4 is a view schematically showing a projection geometry of the ultrasonic treatment instrument according to a first exemplary embodiment, when the proximal side is viewed from the distal side along the longitudinal axis.

As shown in FIGS. 2 to 4, a cover member (protection member) 51 in a cylindrical shape is arranged outside the probe main body 31. The cover member 51 has the inner surface and the outer surface. The cover member 51 covers part of the ultrasonic probe 20. The cover member 51 is extended along the longitudinal axis C to externally cover the probe main body 31 of the ultrasonic probe 20. The cover member 51 is fixed to the distal end portion of the sheath 15. The cover member 51 is supported by the sheath 15.

The cover member 51 is made of, for example, fluorine-based resin. For fluorine-based resin, for example, PFA (perfluoroalkoxy alkane), PTFE (poly tetra fluoro ethylene), or PEEK (polyether ether ketone) is used. The cover member 51 is preferably made of a biocompatible material with a low friction coefficient. The cover member 51 is formed by, for example, cutting or injection molding.

The proximal end portion of the cover member 51 is arranged between the first area 36 of the probe main body 31 and the inner peripheral surface of the distal end portion of the sheath 15. The distal end of the cover member 51 covers the distal end portion of the second area 37 of the probe main body 31. Therefore, the distal end of the cover member 51 is positioned on the further proximal side than the proximal end of the distal-end treatment portion 32. The cover member 51 externally covers both parts of the first area 36 and the second area 37 of the probe main body 31 of the ultrasonic probe 20, thereby exposing the distal-end treatment portion 32 to the outer side.

FIG. 3B is a cross-sectional view taken along line 3B-3B shown in FIG. 3A. As shown in FIG. 3B, gap V is formed in at least part of a range in the longitudinal direction between the outer peripheral surface of the second area 37 of the probe main body 31 of the ultrasonic probe 20 and the cover 51. That is, the outer peripheral surface of the second area 37 of the probe main body 31 of the ultrasonic probe 20 and the cover member 51 are at least partially spaced apart from each other in the longitudinal direction. It is preferable that the gap V be formed entirely between the cover member 51 and the ultrasonic probe 20 in the longitudinal direction. The gap V ranges from, e.g., 0.005 mm to 0.065 mm.

The cover member 51 externally covers the probe main body 31 across its entire perimeter around the longitudinal axis C. The cover member 51 includes a first member (first part) 56 and a second member (second part) 57, in which the first member 56 externally covers the probe main body 31 in a partial range (first range) around the longitudinal axis C, and the second member 57 externally covers the probe main body 31 in a second range different from the first range around longitudinal axis C. The first member 56 and the second member 57 are extended along the entire cover member 51 in the longitudinal direction.

A connection part 58 is formed between the first member 56 and the second member 57. In the connection part 58, the first member 56 and the second member 57 are connected to each other. The connection part 58 is provided along the entire cover member 51 in the longitudinal direction. In the connection part 58, the first member 56 and the second member 57 are connected to each other by, e.g., welding.

The cover member 51 includes a first extended portion 53 and a second extended portion 55 positioned on the distal side relative to the first extended portion 53. The first extended portion 53 forms the proximal end portion of the cover member 51. The first extended portion 53 is provided with a groove 65 which is concaved from the outer peripheral surface of the cover member 51 toward the inner side. As shown in FIG. 3A, length L4 from the distal end of the ultrasonic probe 20 (the distal end of the distal-end treatment portion 32) to the proximal end of the second extended portion 55 is, for example, 20 mm or more. Preferably, length L4 is 35 mm or more.

FIG. 4 is a view showing a projection geometry of the sheath 15, a projection geometry of the second area 37 of the probe main body 31 of the ultrasonic probe 20, a projection geometry of the distal-end treatment portion 32 of the ultrasonic probe 20, and a projection geometry of the second extended portion 55 of the cover member 51 when the proximal side is viewed from the distal side along longitudinal axis C.

As shown in FIG. 4, an outermost edge 44 of the projection geometry of the distal-end treatment portion 32 forms a polygonal shape such as a rectangle when the proximal side is viewed from the distal side along the longitudinal axis C. That is, the distal-end treatment portion 32 is formed in such a manner that the outermost edge 44 forms a rectangle (oblong figure) when the proximal side is viewed from the distal side along the longitudinal axis C. The outermost edge 44 of the distal-end treatment portion 32 defines an outer edge (outer shape) of a bone hole 111 to be described later. In the present embodiment, the outermost edge 44 of the distal-end treatment portion 32 forms a rectangle having short sides of 4 mm and long sides of 5 mm. The outermost edge 44 may form a regular polygon, etc., or a shape other than a polygonal shape. The outermost edge 44 is shaped as appropriate in accordance with a shape of a desired hole (bone hole).

When the proximal side is viewed from the distal side along the longitudinal axis C, the outermost edge 44 of the distal-end treatment portion 32 and an outer edge 42 of the second area 37 of the probe main body 31 are positioned on the inner side relative to the outer edge 40 of the projection geometry of the sheath 15. When the proximal side is viewed from the distal side along the longitudinal axis C, an outer edge 59 of the cover member 51 is positioned on the inner side relative to the outer edge 40 of the projection geometry of the sheath 15.

The second area 37 of the probe main body 31 is formed in such a manner as to be thinner than the distal-end treatment portion 32. Therefore, when the proximal side is viewed from the distal side along the longitudinal axis C, the projection geometry of the second area 37 of the probe main body 31 of the ultrasonic probe 20 is smaller than that of the distal-end treatment portion 32 of the ultrasonic probe 20. With this configuration, when the proximal side is viewed from the distal side along the longitudinal axis C, the outer edge 42 of the projection geometry of the second area 37 of the probe main body 31 of the ultrasonic probe 20 is positioned on the inner side relative to the outermost edge 44 of the projection geometry of the distal-end treatment portion 32 of the ultrasonic probe 20.

The cover member 51 externally covers the second area 37 of the probe main body 31 of the ultrasonic probe 20. Therefore, when the proximal side is viewed from the distal side along the longitudinal axis C, the projection geometry of the second area 37 of the probe main body 31 of the ultrasonic probe 20 is smaller than that of the cover member 51. With this configuration, when the proximal side is viewed from the distal side along the longitudinal axis C, the outer edge 42 of the projection geometry of the second area 37 of the probe main body 31 of the ultrasonic probe 20 is positioned on the inner side relative to the outer edge 59 of the projection geometry of the cover member 51.

In the present embodiment, an outer edge 60 of the projection geometry of the second extended portion 55 of the cover member 51 forms a substantial rectangle when the proximal side is viewed from the distal side along the longitudinal axis C. That is, a cross-sectional shape of the inner surface of the cover member 51 is similar to that of the second area 37 of the probe main body 31 of the ultrasonic probe 20. Furthermore, the second extended portion 55 of the cover member 51 is formed in such a manner as to be thinner than the distal-end treatment portion 32 of the ultrasonic probe 20. Therefore, when the proximal side is viewed from the distal side along the longitudinal axis C, the projection geometry of the second extended portion 55 of the cover member 51 is smaller than that of the distal-end treatment portion 32 of the ultrasonic probe 20. With this configuration, when the proximal side is viewed from the distal side along the longitudinal axis C, the outer edge 60 of the projection geometry of the second extended portion 55 of the cover 51 is positioned on the inner side relative to the outermost edge 44 of the projection geometry of the distal-end treatment portion 32 of the ultrasonic probe 20.

Figure 7:
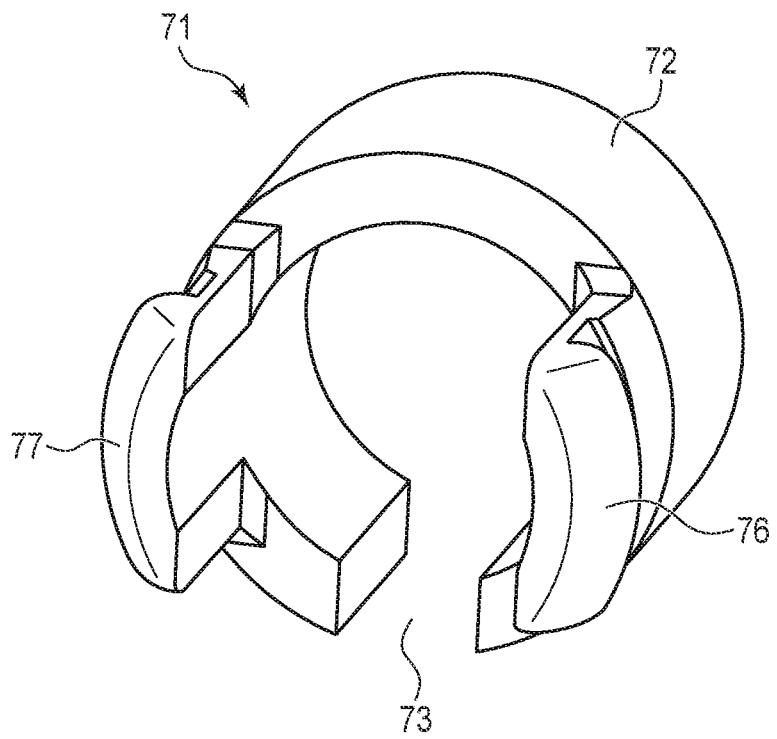
FIG. 7 is a perspective view schematically showing a fixing member of the ultrasonic treatment instrument according to a first exemplary embodiment.

The cover member 51 is attached to the sheath 15 by, for example, a snap-fit structure. In the present embodiment, the cover member 51 is fixed to the distal end portion of the sheath 15 through a fixing member 71 having a snap-fit structure. The fixing member 71 is made of, for example, a resin material. FIG. 7 is a perspective view showing an outer appearance of the fixing member 71.

The fixing member 71 includes a main body (ring portion) 72 and protrusions 76 and 77. The main body 72 has a cut-out portion 73, and is extended around a center axis (longitudinal axis C) to form a substantially C shape. Each of the protrusions 76 and 77 is elongated from the main body 72 toward a side (outer side) away from the distal side and the longitudinal axis C. The protrusions 76 and 77 are arranged on the sides opposite to each other with the center axis (longitudinal axis C) being interposed therebetween.

As shown in FIG. 3A, the main body 72 of the fixing member 71 is fitted into the groove 65 of the cover member 51. By the main body 72 of the fixing member 71 being fitted into the groove 65 of the cover member 51, the fixing member 71 is attached to the cover 51, and the movement is restricted in the longitudinal direction between the fixing member 71 and the cover member 51.

Figure 5:
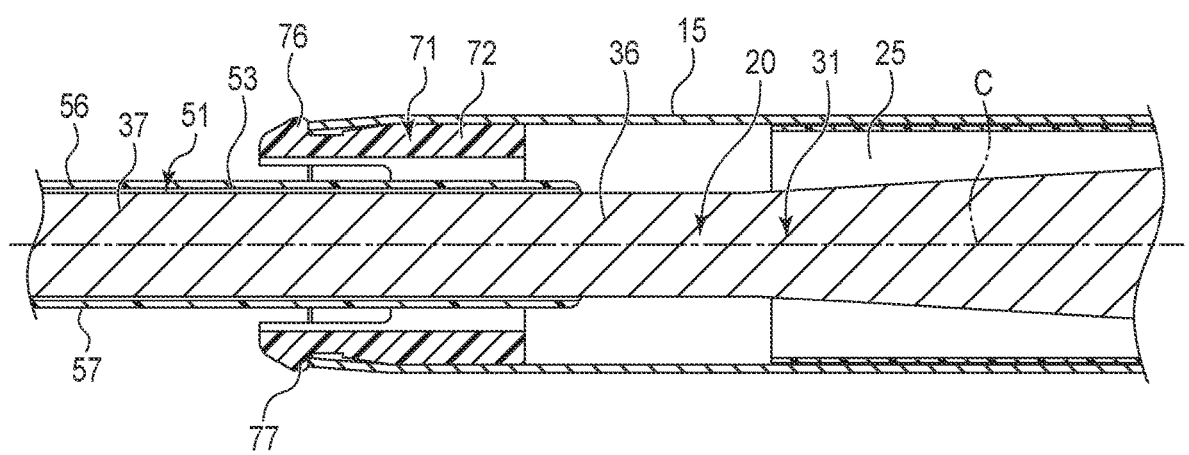
FIG. 5 is a view schematically showing a connection part between a cover and a sheath of the ultrasonic treatment instrument according to a first exemplary embodiment, in a cross section which is parallel or substantially parallel to and also passes through the longitudinal axis.

As shown in FIG. 5, each of the protrusions 76 and 77 protrudes from the distal end of the sheath 15 toward the outer side on the distal side relative to the distal end of the sheath 15. By the protrusions 76 and 77 abutting on the distal end portion of the sheath 15 from the distal side, the movement of the fixing member 71 and the cover member 51 with respect to the sheath 15 is restricted.

The main body 72 is pressed by the sheath 15 in a direction approaching the longitudinal axis C (toward the inner side). The main body 72 is elastically deformed by being pressed by the sheath 15, so that the cut-out portion 73 shrinks as compared with that of the main body 72 not pressed by the sheath 15. The sheath 15 is pressed toward the outer side with respect to longitudinal axis C by an elastic force of the main body 72. With an elastic force of the main body 72, the fixing member 71 is fixed to the sheath 15.

As described above, the fixing member 71 is fixed to the cover member 51. In this manner, by the fixing member 71 being fixed to the sheath 15, the cover member 51 is fixed to the sheath 15 through the fixing member 71.

The protrusions 76 and 77 of the fixing member 71 are spaced apart from the outer peripheral surface of the probe main body 31 of the ultrasonic probe 20. That is, a gap is provided between each of the protrusions 76 and 77 of the fixing member 71 and the outer peripheral surface of the cover member 51. This allows each of the protrusions 76 and 77 to be bent, by their elastic deformation, toward the outer peripheral surface of the cover 51, that is, toward the inner side.

Next, a method of manufacturing the treatment instrument 11 of the ultrasonic treatment assembly 2 including the cover member 51 will be described. To manufacture the treatment instrument 11, first, the ultrasonic probe 20 is attached to the housing 14. At this time, the ultrasonic probe 20 protrudes from the distal end of the housing 14 toward the distal side.

Figure 6:
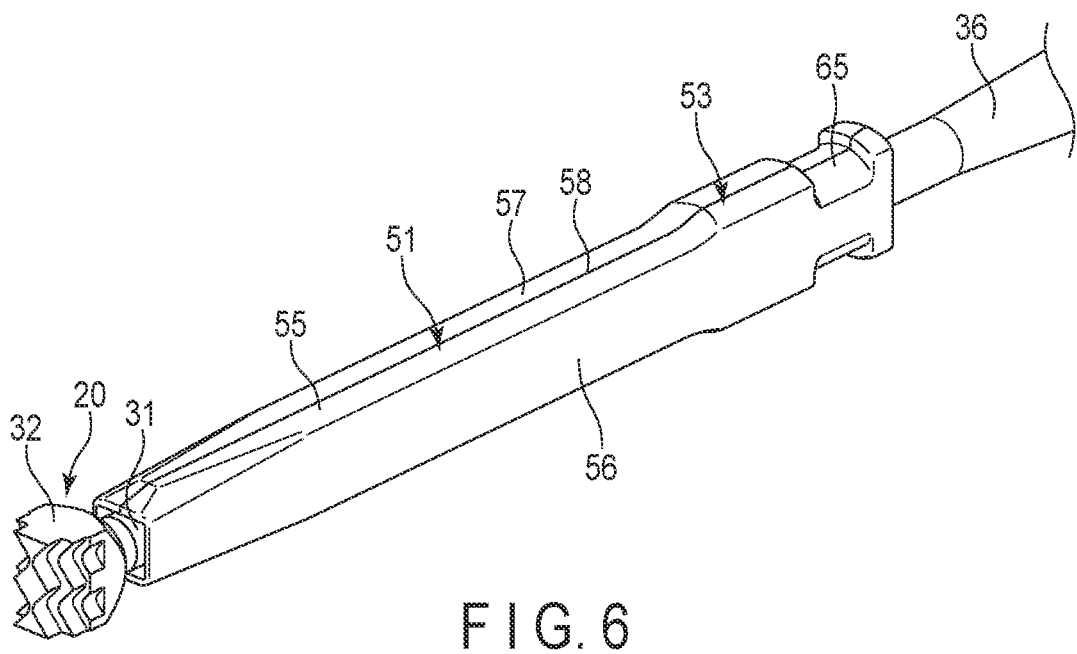
FIG. 6 is a perspective view schematically showing the ultrasonic treatment instrument according to a first exemplary embodiment, having a cover arranged outside the ultrasonic probe.

Next, as shown in FIG. 6, the first member 56 and the second member 57 are arranged outside the second area 37 of the ultrasonic probe 20, from the sides opposite to each other. At this time, the first member 56 and the second member 57 are arranged from the direction intersecting with (perpendicular to or substantially perpendicular to) the longitudinal axis C. Then, the first member 56 and the second member 57 are connected to each other by, for example, welding. This results in the formation of the connection part 58 between the first member 56 and the second member 57, and the first member 56 and the second member 57 form the cover member 51.

Figure 8:
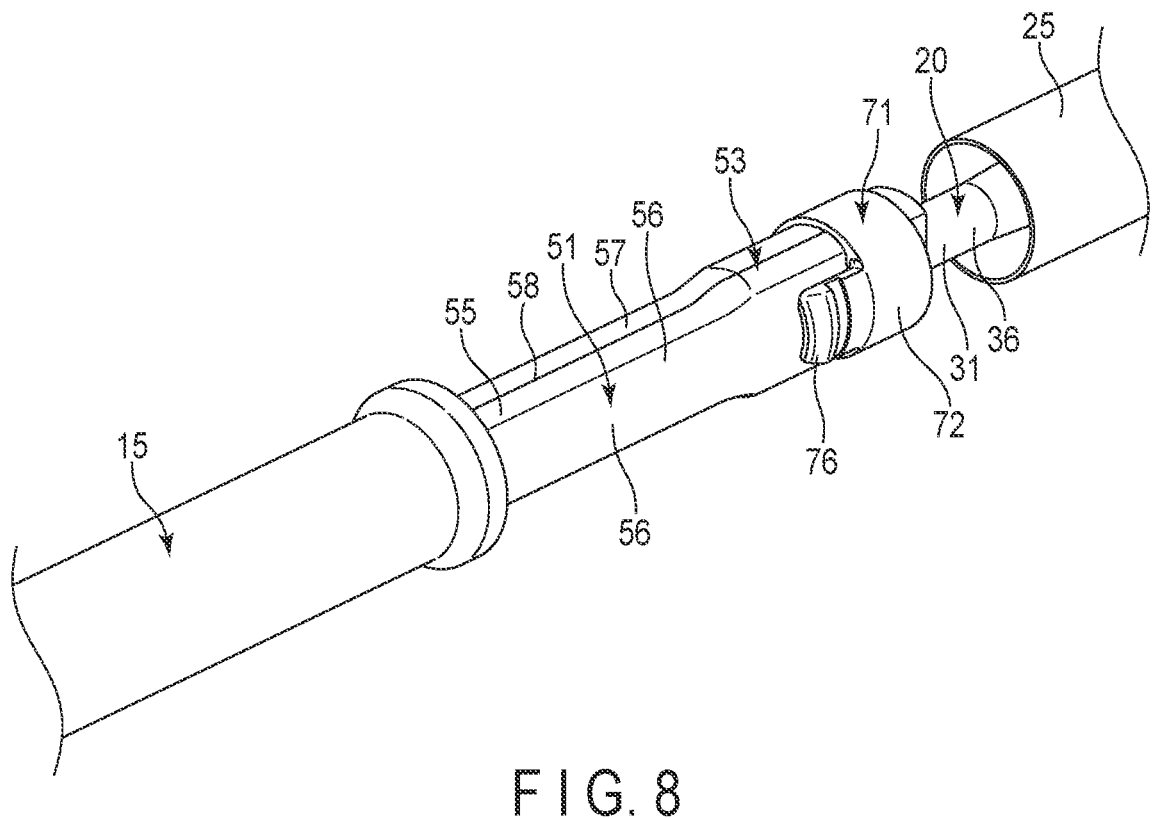
FIG. 8 is a perspective view schematically showing how the cover of the ultrasonic treatment instrument according to a first exemplary embodiment is attached to the sheath.
Figure 9:
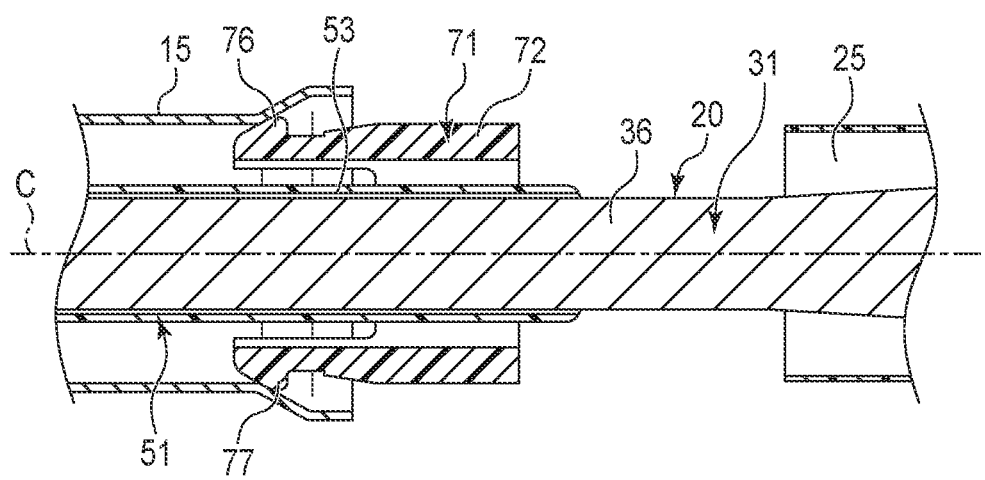
FIG. 9 is a view schematically showing how the cover of the ultrasonic treatment instrument according to a first exemplary embodiment is attached to the sheath, in a cross section which is parallel or substantially parallel to and also passes through the longitudinal axis.
Figure 10:
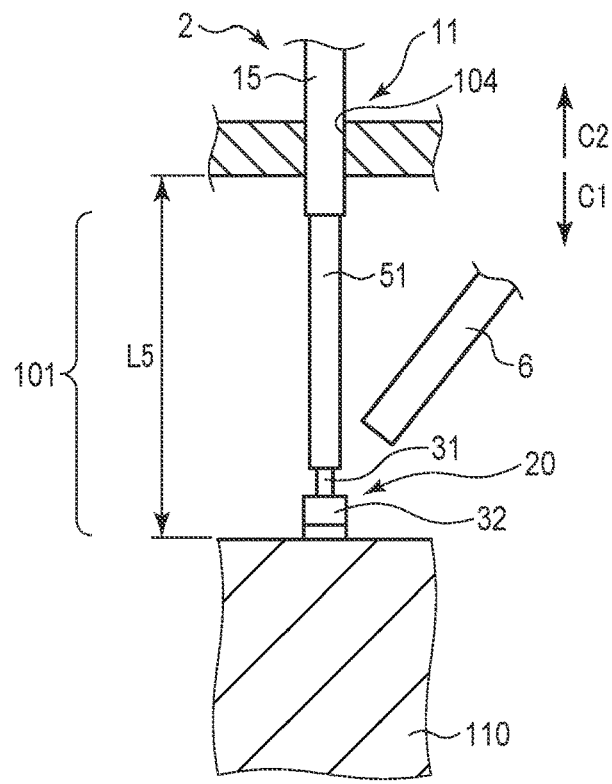
FIG. 10 is a view schematically showing how cutting of a bone is initiated using the ultrasonic treatment instrument according to a first exemplary embodiment.
Figure 11:
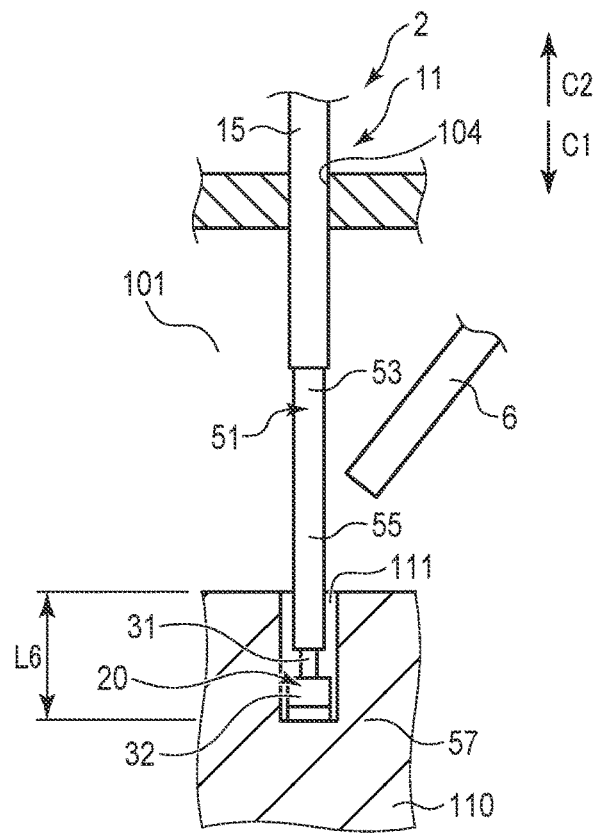
FIG. 11 is a view schematically showing that a bone hole is formed in a bone using the ultrasonic treatment instrument according to a first exemplary embodiment.

Next, as shown in FIGS. 8 and 9, the ultrasonic probe 20 is inserted from the distal end into the inner tube 25. The fixing member 71 is attached to the first extended portion 53 of the cover member 51. The ultrasonic probe 20, the cover member 51, and the fixing member 71 are inserted into the sheath 15, and the sheath 15 is loaded onto the housing 14 from the distal side.

When the ultrasonic probe 20, the cover member 51, and the fixing member 71 are inserted into the sheath 15, the proximal end of the sheath 15 abuts onto the protrusions 76 and 77 of the fixing member 71 from the distal side. As described above, a gap is provided between each of the protrusions 76 and 77 and the outer peripheral surface of the cover member 51. By the protrusions 76 and 77 being pressed by the sheath 15 toward the inner side, they are bent, by their elastic deformation, toward the outer peripheral surface of the cover 51. The sheath 15 moves toward the proximal side with respect to the fixing member 71 while pressing the protrusions 76 and 77 and the main body 72 toward the inner side.

As shown in FIG. 5, when the distal end of the sheath 15 moves to the further proximal side than the protrusions 76 and 77 of the fixing member 71, pressing of the protrusion 76 by the sheath 15 is released. Then the protrusions 76 and 77 move, by an elastic force, in a direction away from the peripheral surface of the cover 51. The sheath 15 is then arranged between the housing 14 and both the protrusions 76 and 77 in the longitudinal direction. This causes the protrusions 76 and 77 to abut onto the distal end portion of the sheath 15 from the distal side, thereby restricting the movement of the fixing member 71 and the cover member 51 with respect to the sheath 15.

Next, the operation of the ultrasonic treatment instrument according to the present embodiment will be described. The ultrasonic treatment instrument according to the present embodiment is used for, for example, anterior crucial ligament reconstruction. Herein, referring to FIGS. 10 and 11, the case in which the bone hole (concave hole) 111 is formed using the treatment system 1 in a bone 110 of a joint cavity 101 within a knee joint will be described as an example.

In this treatment, first, an operator inserts the ultrasonic treatment assembly 2 and the arthroscope 6 into the joint cavity 101 through a portal (dermatome) 104, etc. of the knee joint. The operator then arranges the arthroscope 6 in such a position that the distal-end treatment portion 32 of the ultrasonic probe 20 of the ultrasonic treatment assembly 2 is observable from the proximal side. At this time, the distal end portion of the arthroscope 6 is arranged in the further proximal side than the distal-end treatment portion 32 of the ultrasonic probe 20, that is, in the vicinity of the second area 37 of the probe main body 31. In this way, the distal-end treatment portion 32 is arranged within a visual field of the arthroscope 6 when the distal side is viewed from the proximal side along the longitudinal axis C.

While viewing images obtained with the arthroscope 6 through the monitor 10, the operator arranges the distal end of the distal-end treatment portion 32 of the treatment instrument 11 in the vicinity of a part of the bone 110 in which he or she desires to form the bone hole 111, and aligns a direction in which he or she desires to form the bone hole 111 with the longitudinal axis C of the treatment instrument 11. Herein, length (distance) L5 from the portal 104 to a formation point of the bone hole 111 on the bone 110 is about 60 mm to 70 mm in the case of an average adult male.

As described above, by inputting operation for the power supply 4 to supply electric energy to the ultrasonic treatment assembly 2, ultrasonic vibration generated in the ultrasonic transducer 19 is transmitted to the distal-end treatment portion 32 of the ultrasonic probe 20. The operator brings the distal-end treatment portion 32 into contact with the bone 110 with the distal-end treatment portion 32 being in receipt of transmitted ultrasonic vibration. This initiates cutting of the bone 110. The operator then moves the distal-end treatment portion 32 with respect to the bone 110, from the proximal side toward the distal side in the longitudinal direction. Accordingly, the bone 110 is further cut as the distal-end treatment portion 32 moves, thereby resulting in the formation of the bone hole 111 in the bone 110. A cross-sectional shape of the bone hole 111 is defined by the projection geometry (outermost edge 44) of the distal-end treatment portion 32, and forms the same or substantially same shape as the projection geometry (outermost edge 44) of the distal-end treatment portion 32. Generally, depth (length) L6 of the bone hole 111 is about 10 mm to 35 mm. Note that cutting of the bone 110 is performed with perfusion solution being perfused within the joint cavity 101.

In the present embodiment, length L1 of the protrusion of the ultrasonic probe 20, which protrudes from the distal end of the sheath 15 toward the distal side, is equal to or greater than depth (length) L6 of the bone hole 111. For this reason, a length from the distal end of the ultrasonic probe 20 to the distal end of the sheath 15 is equal to or greater than depth (length) L6 of the bone hole 111. This prevents, when the bone hole 111 is formed in the bone 110, the sheath 15 from interfering with the bone 110, thereby securing the accessibility of the distal-end treatment portion 32 to a part on which a treatment is performed.

In the present embodiment, length L1 of the protrusion of the ultrasonic probe 20, which protrudes from the distal end of the sheath 15 toward the distal side, is equal to or less than length L5 from the portal 104 to the formation point of the bone hole 111 on the bone 110. For this reason, a length from the distal end of the ultrasonic probe 20 to the distal end of the sheath 15 is equal to or less than length L5 from the portal 104 to the formation point of the bone hole 111 on the bone 110. In the formation of the bone hole 111, when the distal-end treatment portion 32 is in contact with the bone 110, the distal end of the sheath 15 is inserted further inside than the portal 104. Therefore, the sheath 15 is arranged between the portal 104 and both the ultrasonic probe 20 and the cover member 51. This prevents both the ultrasonic probe 20 and the cover member 51 from coming into contact with the portal 104 during a treatment. By preventing contact between the portal 104 and both the ultrasonic probe 20 and the cover member 51, the accessibility of the distal-end treatment portion 32 to a part on which a treatment is performed is secured. In addition, by preventing contact between the portal 104 and both the ultrasonic probe 20 and the cover member 51, the portal 104 is prevented from being affected by ultrasonic vibration of the ultrasonic probe 20.

In the present embodiment, the cover member 51 is arranged outside the second area 37 of the probe main body 31 of the ultrasonic probe 20. This prevents another instrument such as the arthroscope 6 from coming into contact by mistake with the second area 37 of the probe main body 31 of the ultrasonic probe 20 during a treatment. This secures the treatment performance by the distal-end treatment portion 32.

In the present embodiment, the cover member 51 is fixed to the distal end portion of the sheath 15, and the gap V is formed between the cover 51 member and the ultrasonic probe 20. This prevents the cover member 51 from coming into contact with the ultrasonic probe 20. The cover member 51 and the ultrasonic probe 20 are prevented from coming into contact with each other, and this prevents the occurrence of deviation in a resonance frequency of ultrasonic vibration due to contact between the cover member 51 and the ultrasonic probe 20, and the occurrence of friction heat between the cover member 51 and the ultrasonic probe 20. Accordingly, a decrease in the treatment performance by the distal-end treatment portion 32 can be prevented. The cover member 51 in the present embodiment is made of a material having flexibility, such as fluorine-based resin. This prevents, even in the case where the cover 51 and the ultrasonic probe 20 come into contact with each other during a treatment, the occurrence of deviation in a resonance frequency of ultrasonic vibration due to contact between the cover member 51 and the ultrasonic probe 20.

Furthermore, in the present embodiment, the second extended portion 55 of the cover member 51 is formed in such a manner as to be thinner than the distal-end treatment portion 32 of the ultrasonic probe 20. With this configuration, when the proximal side is viewed from the distal side along the longitudinal axis C, the outer edge 60 of the projection geometry of the second extended portion 55 of the cover 51 is positioned on the inner side relative to the outermost edge 44 of the projection geometry of the distal-end treatment portion 32 of the ultrasonic probe 20. Furthermore, the outermost edge 44 of the distal-end treatment portion 32 defines the outer edge (outer shape) of the bone hole 111 formed in the bone 110. That is, the second extended portion 55 of the cover member 51 is formed in such a manner as to be smaller than the outer edge (outer shape) of the bone hole 111 to be formed. This enables, when the bone hole 111 is formed in the bone 110, the second extended portion 55 of the cover member 51 to be inserted into the bone hole 111 without coming into contact with the bone 110 if the distal-end treatment portion 32 travels to the bone 110 in a straight line or substantially straight line along the longitudinal axis C. This prevents the cover member 51 from coming into contact with the bone 110 at the time of a treatment, thereby securing the accessibility of the distal-end treatment portion 32 during the treatment.

The cover member 51 is formed in such a manner that at least a part thereof which is to be inserted into the bone hole 111 to be formed is thinner than the distal-end treatment portion 32.

In the present embodiment, the cover member 51 is formed by connecting the first member 56 and the second member 57 to each other. That is, the cover member 51 in the present embodiment is formed by connecting a plurality of separate members. This enables easy attachment of the cover member 51 to the ultrasonic probe 20 even in the case where the ultrasonic probe 20 cannot be inserted into the cover member 51 from the distal-end treatment portion 32 due to the fact that the cover member 51 is formed in such a manner as to be thinner than the distal-end treatment portion 32.

Figure 12:
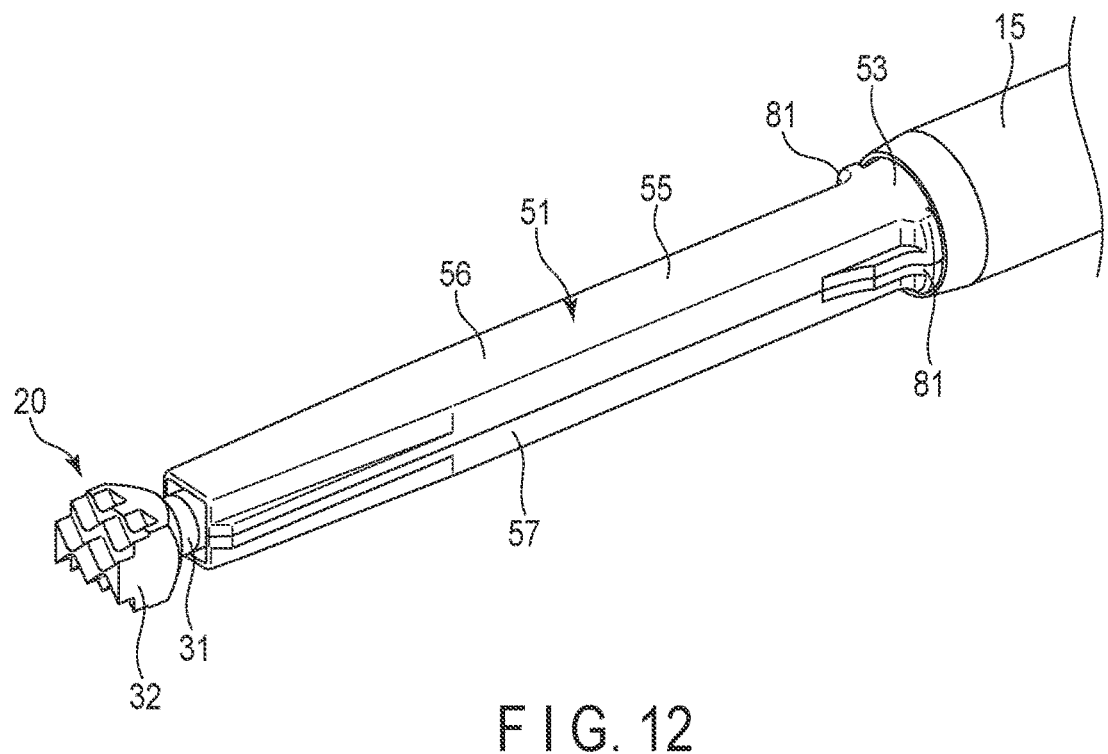
FIG. 12 is a perspective view schematically showing a distal end portion of an ultrasonic treatment instrument according to a first exemplary embodiment.
Figure 13:
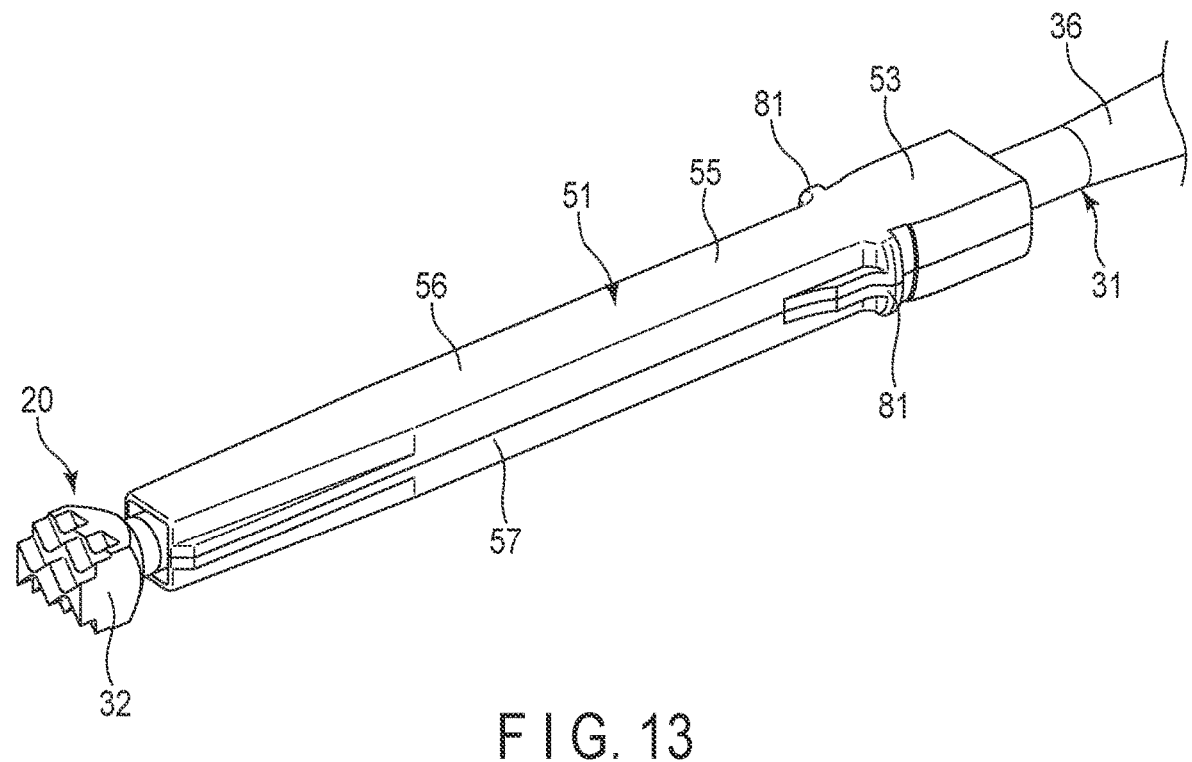
FIG. 13 is a perspective view schematically showing the ultrasonic treatment instrument according to a second exemplary embodiment, having a cover arranged outside an ultrasonic probe.

Second exemplary embodiment will be described with reference to FIGS. 12 and 13. In the present embodiment, the cover member 51 is fixed directly to the distal end portion of the sheath 15. In the present embodiment, the cover member 51 includes a protrusion 81 as shown in FIGS. 12 and 13. The protrusion 81 is elongated from the outer peripheral surface of the first extended portion 53 toward the outer side. On the further distal side than the distal end of the sheath 15, the protrusion 81 protrudes outside the outer peripheral surface of the sheath 15. By providing the protrusion 81, the movement of the cover member 51 toward the proximal side with respect to the sheath 15 is restricted.

The protrusion 81 is elastically deformable and is thus flexible with respect to the first extended portion 53. In the present embodiment, the protrusion 81 functions as a snap-fit structure when the cover 51 is fixed to the sheath 15.

Figure 14:
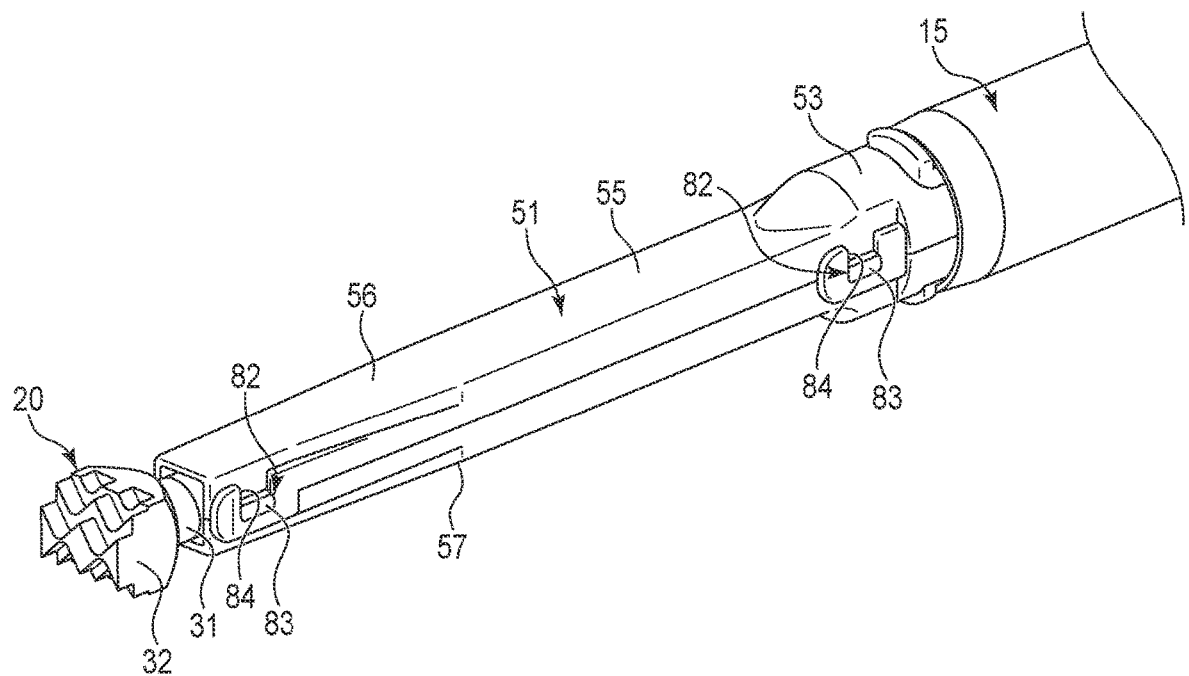
FIG. 14 is a perspective view schematically showing a distal end portion of an ultrasonic treatment instrument according to a third exemplary embodiment.

Third exemplary embodiment will be described with reference to FIG. 14. In the present embodiment, the first member 56 and the second member 57 of the cover member 51 are connected to each other by the snap-fit structure. The cover member 51 includes a plurality of connection parts 82 each connecting the first member 56 and the second member 57. The connection parts 82 are respectively provided in the distal end portion and the proximal end portion of the cover member 51. In each of the connection parts 82, the second member 57 is provided with protrusions 83 protruding outwardly, and the first member 56 is provided with fitting holes 84 into which the protrusions 83 can respectively be fitted. By the protrusions 83 being respectively engaged with the corresponding fitting holes 84 from their insides, the first member 56 and the second member 57 are connected to each other, thereby forming the cover member 51.

The cover member 51 is made of a material having a flexibility, such as fluorine-based resin. Therefore, the protrusions 83 and the fitting holes 84 function as the snap-fit structure when the first member 56 and the second member 57 are connected to each other.

Figure 15:
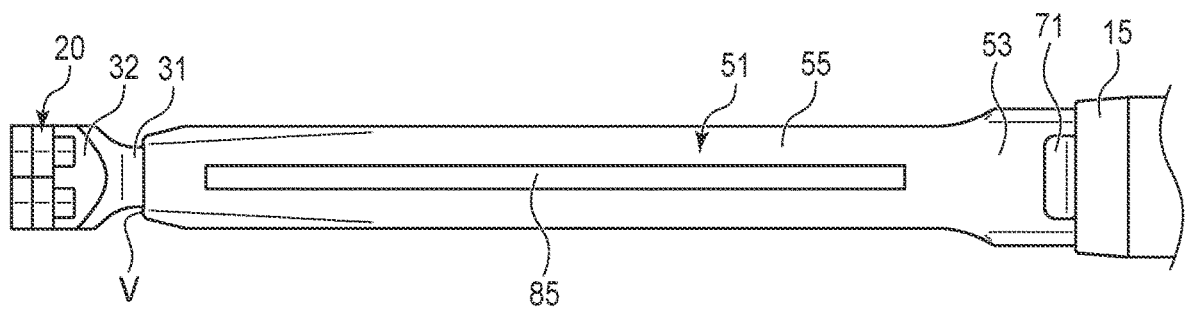
FIG. 15 is a schematic view of a distal end portion of an ultrasonic treatment instrument according to a fourth exemplary embodiment when viewed from one side in a direction intersecting with a longitudinal axis.

Fourth exemplary embodiment will be described with reference to FIG. 15. As shown in FIG. 15, in the present embodiment, the cover 51 includes a slit (through-hole) 85. The slit 85 allows the inside of the cover member 51 to communicate with the outside. The slit 85 is extended in the longitudinal direction. A plurality of slits 85 may be arranged in different positions around the longitudinal axis C.

In the present embodiment, by the slit 85 being provided, the inside of the cover member 51 communicates with the outside through the slit 85. Accordingly, even if shavings (bone fragments) caused by cutting the bone 110, heat caused by cutting, and the like flow from the distal side into the gap V between the cover member 51 and the ultrasonic probe 20, they are discharged to the outside of the cover member 51 through the slit 85. This prevents the treatment performance from being affected by shavings or heat flowing into the gap V between the cover member 51 and the ultrasonic probe 20.

Figure 16:
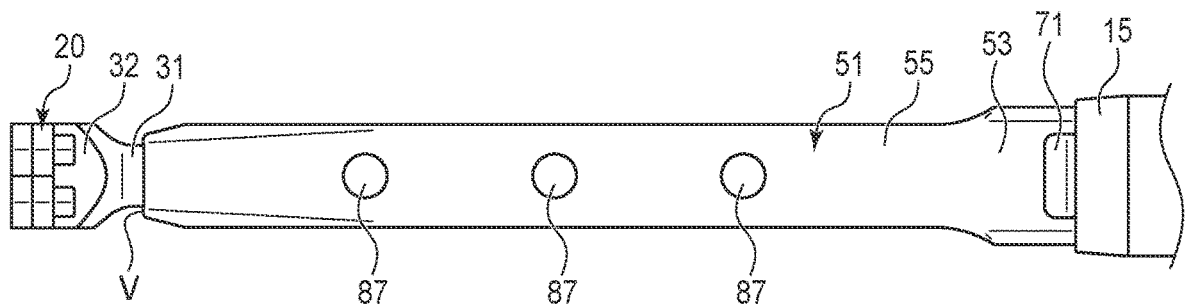
FIG. 16 is a schematic view of a distal end portion of an ultrasonic treatment instrument according to a fifth exemplary embodiment when viewed from one side in a direction intersecting with a longitudinal axis.

Fifth exemplary embodiment will be described with reference to FIG. 16. As shown in FIG. 16, in the present embodiment, the cover member 51 includes a plurality of through-holes 87. Each of the through-holes 87 forms substantially a circular shape and allows the inside of the cover member 51 to communicate with the outside. The through-holes 87 are arranged in line in the longitudinal direction. The through-holes 87 may be arranged in line around the longitudinal axis C.

In the present embodiment also, by providing the through-holes 87 in the cover member 51, shaving or heat flowing into the gap V between the cover member 51 and the ultrasonic probe 20 can be discharged to the outside of the cover member 51 through the through-holes 87.

Figure 17:
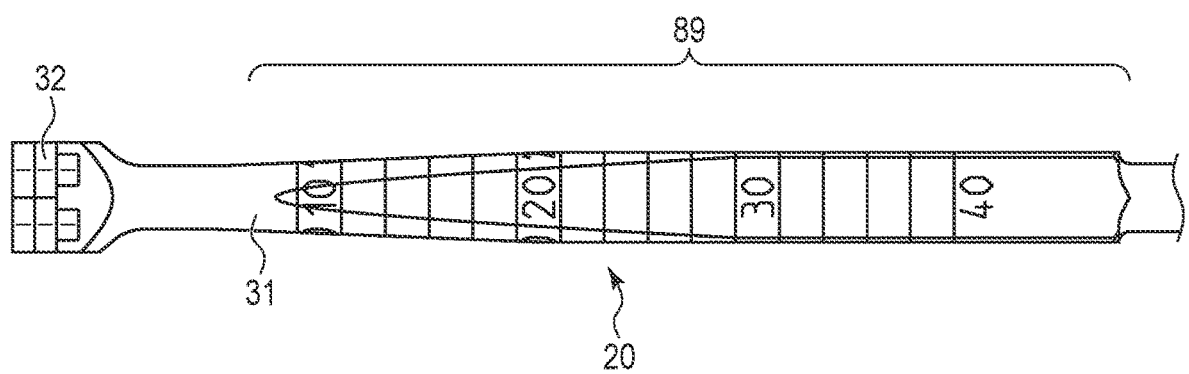
FIG. 17 is a schematic view of a distal end portion of an ultrasonic treatment instrument according to a sixth exemplary embodiment when viewed from one side in a direction intersecting with a longitudinal axis.

Sixth exemplary embodiment will be described with reference to FIG. 17. As shown in FIG. 17, in the present embodiment, the probe main body 31 of the ultrasonic probe 20 is provided with a scale (index) 89 which marks a distance from the distal end of the ultrasonic probe 20. In the present embodiment, it is preferable that the cover member 51 be formed transparently or translucently. In such a case, the scale 89 is observable through the arthroscope 6 and the monitor 10. The scale 89 may be provided in the outer peripheral surface of the cover member 51.

Herein, when the bone hole 111 is formed in the bone 110, depth (length) L6 of the bone hole 111 becomes equal or approximately equal to the length of a part of the ultrasonic probe 20 which has been inserted into the bone hole 111. Therefore, when forming the bone hole 111 in the bone 110, an operator can continuously perceive depth (length) L6 of the formed bone hole 111 by reading the scale 89 in the vicinity of an entry into the bone hole 111 using the arthroscope 6 and the monitor 10.

(Common Structure Among Embodiments)

An ultrasonic transmitter unit (11) includes: a sheath (15) that forms a cylindrical shape and is having a proximal end and a distal end; an ultrasonic transmitter (20) configured to be inserted into the sheath (15); and a cover member (51) that covers a part of the ultrasonic transmitter (20) and has an inner surface and an outer surface. The ultrasonic transmitter (20) includes: a first area (36) surrounded by the sheath (15); a second area (37) protruding from the distal end of the sheath (15); and a distal-end treatment portion (32) provided in a distal end of the second area (37). The cover member (51) covers the second area (37) of the ultrasonic transmitter (20), and exposes the distal-end treatment portion (32) of the ultrasonic transmitter (20) to an outside, and is made of fluorine-based resin.

The present invention is not limited to the above embodiments, and can be modified in various manners in practice when implementing the invention without departing from the gist of the invention. The respective embodiments may be appropriately combined to the extent possible, in which case a combined effect will be obtained. Furthermore, the above embodiments include various stages of invention, and various inventions can be derived by appropriately combining the disclosed elements.

The invention claimed is:

1. An ultrasonic transmitter unit comprising:
a sheath that forms a cylindrical shape and has a proximal end and a distal end;
an ultrasonic transmitter configured to be inserted into the sheath; and
a cover member being fixed to a distal end portion of the sheath, and covering a part of the ultrasonic transmitter, the cover member having an inner surface and an outer surface, wherein:
the ultrasonic transmitter includes:
a first area surrounded by the sheath;
a second area protruding from the distal end of the sheath; and
a distal-end treatment portion provided in a distal end of the second area,
the cover member covers the second area of the ultrasonic transmitter such that the distal-end treatment portion of the ultrasonic transmitter is exposed;
the cover member is made of fluorine-based resin; and
a gap is formed in a direction along a longitudinal axis between the cover member and the second area of the ultrasonic transmitter along an entire length of the cover.

2. The ultrasonic transmitter unit according to claim 1, wherein a projection geometry of the cover member falls within a perimeter of a projection geometry of the distal-end treatment portion when viewed from a distal end of the cover member along a longitudinal axis.

3. The ultrasonic transmitter unit according to claim 1, wherein a projection geometry of the cover member is provided within an inner surface of the sheath when viewed from a distal end of the cover member along a longitudinal axis.

4. The ultrasonic transmitter unit according to claim 1, wherein the cover member includes a through-hole configured to allow communication between the inner surface and the outer surface.

5. The ultrasonic transmitter unit according to claim 1, wherein:
the cover member is configured to cover an entire perimeter of the ultrasonic transmitter about a longitudinal axis; and
the cover member includes a first member provided at a first section that extends along the longitudinal axis, a second member provided at a second section different from the first section, and a connection part configured to connect the first member to the second member.

6. The ultrasonic transmitter unit according to claim 1, wherein a cross-sectional shape of the inner surface of the cover member is similar to a cross-sectional shape of the second area.

7. The ultrasonic transmitter unit according to claim 2, wherein the distal-end treatment portion is shaped as a rectangle.

8. The ultrasonic transmitter unit according to claim 1, wherein a width of the gap is 0.005 mm to 0.065 mm.

9. An ultrasonic transmitter unit comprising:
a sheath that forms a cylindrical shape and has a proximal end and a distal end;
an ultrasonic transmitter configured to be inserted into the sheath; and
a cover member being fixed to a distal end portion of the sheath, and covering a part of the ultrasonic transmitter, the cover member having an inner surface and an outer surface, wherein:
the ultrasonic transmitter includes:
a first area surrounded by the sheath;
a second area protruding from the distal end of the sheath; and
a distal-end treatment portion provided in a distal end of the second area,
the cover member covers the second area of the ultrasonic transmitter such that the distal-end treatment portion of the ultrasonic transmitter is exposed;
the cover member is made of fluorine-based resin;
a gap is formed in a direction along a longitudinal axis between the cover member and the second area of the ultrasonic transmitter along a portion of a length of the cover member; and
a projection geometry of the cover member falls within a perimeter of a projection geometry of the distal-end treatment portion when viewed from a distal end of the cover member along a longitudinal axis.

10. The ultrasonic transmitter unit according to claim 9, wherein the distal-end treatment portion is shaped as a rectangle.

11. The ultrasonic transmitter unit according to claim 9, wherein a projection geometry of the cover member falls within a perimeter of a projection geometry of the distal-end treatment portion when viewed from a distal end of the cover member along a longitudinal axis.

12. The ultrasonic transmitter unit according to claim 9, wherein a projection geometry of the cover member is provided within an inner surface of the sheath when viewed from a distal end of the cover member along a longitudinal axis.

13. The ultrasonic transmitter unit according to claim 9, wherein the cover member includes a through-hole configured to allow communication between the inner surface and the outer surface.

14. The ultrasonic transmitter unit according to claim 9, wherein:
the cover member is configured to cover an entire perimeter of the ultrasonic transmitter about a longitudinal axis; and
the cover member includes a first member provided at a first section that extends along the longitudinal axis, a second member provided at a second section different from the first section, and a connection part configured to connect the first member to the second member.

15. The ultrasonic transmitter unit according to claim 9, wherein a cross-sectional shape of the inner surface of the cover member is similar to a cross-sectional shape of the second area.

* * * * *